(12) United States Patent
Bricker et al.

(10) Patent No.: US 8,071,820 B2
(45) Date of Patent: Dec. 6, 2011

(54) METHOD FOR CONVERTING GLYCEROL TO PROPANOL

(75) Inventors: Maureen L. Bricker, Buffalo Grove, IL (US); Laura E. Leonard, Oak Park, IL (US)

(73) Assignee: UOP LLC, Des Plaines, IL (US)

( * ) Notice: Subject to any disclaimer, the term of this patent is extended or adjusted under 35 U.S.C. 154(b) by 422 days.

(21) Appl. No.: 12/342,728

(22) Filed: Dec. 23, 2008

(65) Prior Publication Data

US 2010/0137654 A1    Jun. 3, 2010

(51) Int. Cl.
*C07C 31/20* (2006.01)
*B01J 19/00* (2006.01)

(52) U.S. Cl. .................. 568/852; 568/868; 422/236
(58) Field of Classification Search .................. 568/852, 568/868; 422/129
See application file for complete search history.

(56) References Cited

U.S. PATENT DOCUMENTS

2008/0274019 A1 * 11/2008 Beggin et al. ................. 422/129
* cited by examiner

*Primary Examiner* — Sikarl Witherspoon
(74) *Attorney, Agent, or Firm* — David J Piasecki

(57) ABSTRACT

A method and apparatus for converting glycerol into propylene glycol by directing a basic glycerol containing feed and a hydrogen containing gas into a reaction zone including a fixed bed of catalyst that is operating at glycerol conversion conditions where the reactor includes and at least one quench zone and directing a quench material into the quench zone.

18 Claims, 4 Drawing Sheets

US 8,071,820 B2

METHOD FOR CONVERTING GLYCEROL TO PROPANOL

BACKGROUND OF THE INVENTION (1) Field of the Invention

This invention concerns methods and apparatuses for controlling the temperature of a glycerol hydrogenolysis reactor to maximize propylene glycol yield while minimizing the creation of undesirable by-products.

(2) Description of the Art

The production of biodiesel utilizes vegetable oils, fats and waste restaurant greases while reducing the U.S. dependence on foreign crude oil. Biodiesel is a renewable, alternative fuel that reduces particulate matter and hydrocarbon emissions. However, for every 9 kilograms of biodiesel produced, about 1 kilogram of a crude glycerol by-product is formed.

A problem that results from refining this crude glycerol into refined glycerol is that the glycerol market cannot absorb it. With plentiful glycerol available, its price and U.S. exports have declined. As a result, much of the crude glycerol by-product of biodiesel production is currently disposed of or is sold at a very minimal price.

This problem may continue to worsen because the U.S. production of biodiesel is expected to continue to grow with a target of 400 million gallons of production by the year 2012. At this production capacity, 3.5 million gallons of crude glycerol will be produced every year. This crude glycerol can be purified by several steps including vacuum distillation to produce USP grade glycerol. However, refining the crude glycerol is complex and expensive.

A problem with crude glycerol from a biodiesel plant is that it requires costly upgrading to achieve a technical grade or USP grade glycerol. Typically, biodiesel producers will acidulate the crude glycerol to remove fatty acids in order to facilitate methanol recovery and recycle. Additional steps must be taken to convert the crude glycerol into a high purity glycerol such as USP glycerol. These additional process steps—which increase the cost of producing USP glycerol—may include ion exchange and/or fractionation. There would be significant operating and capital cost incentives if biodiesel derived glycerol could be sold at a profit as a lower grade product or feedstock such as acidulated glycerol rather than requiring purification.

Glycerol can be converted into propylene glycol by well known methods such as hydrogenolysis. Propylene glycol is a major commodity chemical with a growing market and with an annual production of over 1 billion pounds in the U.S. alone. Some typical uses of propylene glycol are in unsaturated polyester resins, functional fluids (antifreeze, de-icing, and heat transfer), pharmaceuticals, foods, cosmetics, liquid detergents, tobacco humectants, flavors and fragrances, personal care, paints and animal feed.

Today, biodiesel production plants are in need of methods to realize increased income from this crude glycerol byproduct. If crude natural glycerol could be efficiently converted to propylene glycol, this technology could be used in biodiesel production plants to increase profitability. There is a need, therefore, for improvements to existing glycerol to propylene glycol processes so that the processes can operate efficiently and economically using glycerol feedstocks including glycerol feedstocks that have been minimally upgraded.

SUMMARY OF THE INVENTION

The present invention provides improved glycerol conversion processes that include reactors that are able to operate at a lower temperature regime to thereby improve propylene glycol selectivity while decreasing the selectivity of the reaction towards unwanted by-products.

One aspect of this invention is an apparatus for converting glycerol into propylene glycol comprising: a feed stream comprising the combination of a hydrogen containing gas and a glycerol feed including at least 30 wt % glycerol; a reactor including at least two catalyst beds wherein at least one quench mixing zone is positioned between two adjacent catalyst beds; and a conduit for directing a quench material into the quench mixing zone.

Another aspect of this invention are methods for converting glycerol into propylene glycol comprising the steps of: directing a basic glycerol containing feed stream and a hydrogen containing gas to a reaction zone including a fixed bed of catalyst and at least one quench zone wherein the reactor operates at glycerol conversion conditions sufficient to form a reaction zone product including propylene glycol; and directing a quench material into the quench zone.

DETAILED DESCRIPTION OF THE INVENTION

Figure 1:
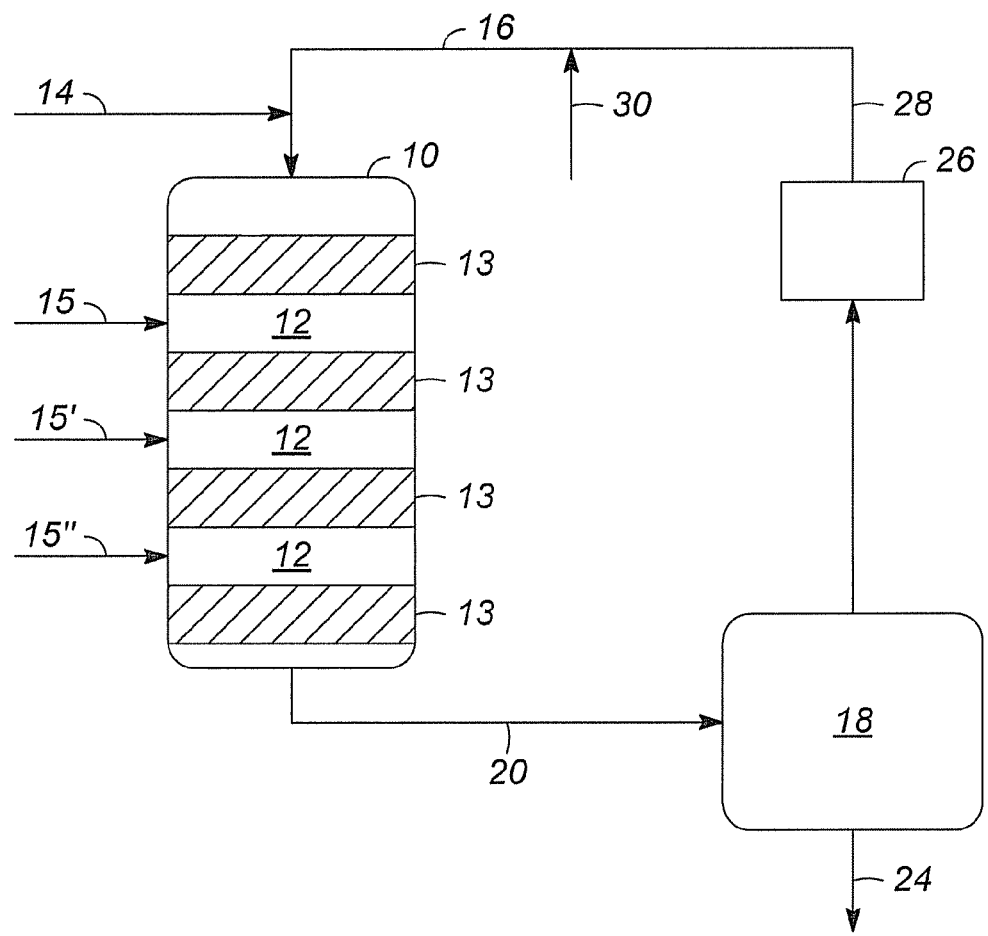
FIG. 1 is a schematic of a process embodiment of this invention including a reactor having multiple quench zones.

The present invention relates to processes and apparatuses for converting glycerol into propylene glycol. Referring now to FIG. 1 there is shown a glycerol conversion process including a fixed catalyst bed reactor 10 having at least two catalyst beds 13 and at least one quench mixing zone 12 separating catalyst beds 13. In FIG. 1, the reactor includes three quench mixing zones 12, 12' and 12". A basic glycerol feed 14 is combined with hydrogen containing gas stream 16 and heated to the desired reaction temperature. The heated combined feed is directed into reactor 10 and into contact with at least one hydrogenolysis catalyst at glycerol conversion pressure, temperature and space velocity conditions to form a reactor product stream 20 that includes propylene glycol. In addition to reactor 10, the process shown in FIG. 1 also includes high pressure separator 18. Reactor product stream 20 is directed into high pressure separator 18 where it is separated into a hydrogen rich gas stream and a liquid product stream 24 that includes propylene glycol. The hydrogen rich gas stream 22 is compressed in recycle compressor 26 to form a compressed recycle gas stream 28. Make up hydrogen 30 is combined with compressed recycle gas stream 28 to form hydrogen containing gas stream 16. The make-up hydrogen is added to the process to replace reacted hydrogen.

The make-up hydrogen containing gas may be any hydrogen rich gas stream that is available at the process site. The make-up hydrogen containing gas should include at least about 70 wt % hydrogen and preferably at least about 85% hydrogen and most preferably at least 95% hydrogen. Moreover, the make-up hydrogen containing gas can be pure hydrogen. Finally, the make up hydrogen containing gas should be free of compounds and impurities that could have an impact on catalyst activity and/or reaction selectivity.

Reactor 10 is loaded with a solid catalyst. Any catalyst that is known to be useful in converting glycerol to propylene glycol in the presence of hydrogen may be loaded into reactor 10. Examples of useful catalysts include copper/chromite; copper zinc and copper oxide with BaO, MgO, CaO, and Mo as additives for activity or stability; mixtures of cobalt, copper, manganese and molybdenum. More preferred catalysts are heterogeneous catalysts such as CoPdRe or NiRe on a solid support such as carbon wherein the metals are reduced. Examples of some useful catalysts are disclosed in U.S. Pat. Nos. 6,479,713, 7,038,094; 6,982,328; 6,900,361; 6,841,085; 6,677,385, 6,570,043; the specifications of each of which are incorporated herein by reference. Particularly preferred catalysts are those disclosed in U.S. patent application Ser. No. 12/082,997, the specification of which is also incorporated herein by reference.

The glycerol feed is typically an aqueous glycerol feed. The aqueous glycerol feed will typically include from about 20 to about 80 wt % glycerol and preferably from about 40 to about 60 wt % glycerol with the remainder being mainly water. While any type of glycerol containing feed may be used in the present invention, there are several general types of glycerol feed that may be directed to the reaction zone— United States Pharmacopia grade (USP) glycerol, technical grade glycerol, food grade glycerol and acidulated crude glycerol. Moreover, the glycerol feed is adjusted to a basic pH and preferably a pH of greater than about 10 and more preferably to a pH of about 12 by the addition of a base such as NaOH or KOH.

The basic glycerol feed is combined with hydrogen, heated to reaction temperatures and directed to fixed bed reactor 10. Reactor 10 is operated and glycerol conversion conditions including include reactor temperatures of between 300° F. and 500° F., and preferably between 325° F. and 400° F. The reactor catalyst volume will be sufficient to achieve a liquid hourly space velocity (LHSV) of glycerol of 0.1-5.0 hr$^{-1}$ based upon the selected glycerol feed rate. The reaction conditions further include a reactor pressure of from about 400 to about 2400 psig. The hydrogen rate to the reactor is typically about 2-20 mole hydrogen per mole glycerol feed into reactor 10.

The conversion of glycerol into propylene glycol is an exothermic reaction. Thus the reactor product outlet temperature will generally be greater than the temperature of the combined feed directed to reactor 10. It has been found that carefully controlling the process conditions such as temperature in the fixed bed reactor can lead to optimal catalyst performance in terms of the selectivity to propylene glycol and glycerol conversion as well as the byproducts produced. Minimizing the byproduct production is critical for minimizing the capital and operations costs of the reaction product purification system. Two of the major byproducts, ethylene glycol and 2,3-butanediol, have boiling points very close to propylene glycol. Therefore, minimizing their production minimizes the sizes of vessels such as fractionation columns needed in the purification system to separate the by-products from the propylene glycol product.

The current invention includes a reactor 10 designed to optimize the glycerol conversion to propylene glycol while simultaneously minimizing the byproduct production, most notably ethylene glycol and butanediols by using one or more quench mixing zones 12. Reactor 10 further includes at least one and preferably a plurality of quench mixing zones 12. Each quench mixing zone 12 includes a quench stream 15 that is directed into the quench mixing zone 12 located between adjacent catalyst beds 13.

The quench material may be either gas or liquid. Useful gases include but are not limited to make up hydrogen gas, recycle hydrogen gas, a combination of make up hydrogen and recycle hydrogen gas and any other gas streams that are readily available on the process site. A preferred quench gas is hydrogen because of its availability in the process. In order to use hydrogen as a quench gas, the recycle compressor would need to be larger and the compressed recycle hydrogen containing gas would be a source of the hydrogen gas. An alternative source for the hydrogen quench gas would be the make-up hydrogen gas. In this process embodiment, the make-up hydrogen gas would be initially directed into the process at the one or more quench zones 12.

Alternatively, a liquid process stream could be used as quench. Such liquid process streams including, but are not limited to fresh feed, water (recycled from the product purification section), unconverted glycerol recovered in the fractionation section, recycling the liquid product from the high pressure separator, or any other liquid product or byproduct stream recovered in the separation section.

The number of catalyst beds 13 and quench zones 12 required in reactor 10 will vary depending upon the degree of temperature control that is desired across each catalyst bed 13. Generally, the temperature increase across each catalyst that will be controlled at about 10 to about 80° F. More preferably the catalyst temperature increase will be controlled so that it is no greater than from about 10 to about 40° F. One skilled in the art would readily understand that the temperature differential across catalyst beds 13 can be controlled both by the volume of quench stream that is being directed into quench mixing zones 12 and by designing the height of catalyst beds 13 to insure that the amount of design quench is capable of controlling the temperature increase across the reactor catalyst bed 13 in the desired range.

Quench stream 15 is injected into quench mixing zones 12 so that it can combine with intermediate reaction products and be uniformly distributed over the subsequent catalyst beds 13. In order to improve vapor and liquid distribution, quench mixing zones 12 may include liquid and gas distributors. The quenching of the reactor intermediate products between catalyst beds allows the reactor temperature to be closely controlled in order to prevent portions of the reactor from operating at high temperatures, such as temperatures substantially greater than about 375° F. at which potentially detrimental increases in byproduct conversion can begin to occur.

In order to increase the glycerol conversion while operating at lower temperature the catalyst volume can be increased. This can be achieved by making the reactor fixed catalyst bed larger and/or by operating the reactor at a low glycerol LHSV. For a fixed catalyst bed size, a lower LHSV means less glycerol throughput.

EXAMPLE 1

A. Catalyst Preparation

A Co/Pd/Re catalyst including 2.5 wt % Co, 0.4 wt % Pd, and 2.4 wt % Re on Norit ROX 0.8—an acid washed extruded steam activated carbon—was prepared using the catalyst preparation examples from U.S. patent application Ser. No. 12/082,997, the specification of which is incorporated herein by reference. The catalyst was reduced at 320° C. under $H_2$ prior to use.

B. Pilot Plant Operation

Glycerol hydrogenolysis tests were performed using the catalysts prepared above in a pilot plant. The pilot plant included a single reactor. The catalyst (150 cc) was loaded into the reactor with an inert solid diluent material (95 cc) to dilute the bed. The purpose of the diluent is to lengthen the catalyst bed to improve the flow characteristics through the bed and to spread the heat of reaction allowing the reactor to operate more isothermally. The catalyst bed was topped with 40 cc of inert material to act as a preheat section.

The reactor was operated in a once through feed mode—the glycerol feed was combined with pure header hydrogen and sent to the reactor. The glycerol feeds used in the various examples are set forth in Table 1 below:

TABLE 1

| Feedstock # | | 1 |
|---|---|---|
| Composition | Units | USP Glycerol |
| Sodium Sulfate | wt % | 0.00 |
| Water | wt % | 58.9 |
| NaOH | wt % | 1.0 |
| Glycerol | wt % | 40.1 |
| Total | wt % | 100.0 |

The glycerol feed was adjusted to a pH of about 12 using NaOH prior to use.

The pilot plant reactor temperature was controlled by submerging the reactor in a continuously stirred bath. The reactor effluent was directed to a high pressure separator operating at the reactor pressure which separated the un-dissolved gas from the liquid phase. The rate of the gas stream exiting the high pressure separator was measured with a wet test meter. The liquid leaving the HPS was collected as the liquid product for analysis.

EXAMPLE 2

Figure 2:
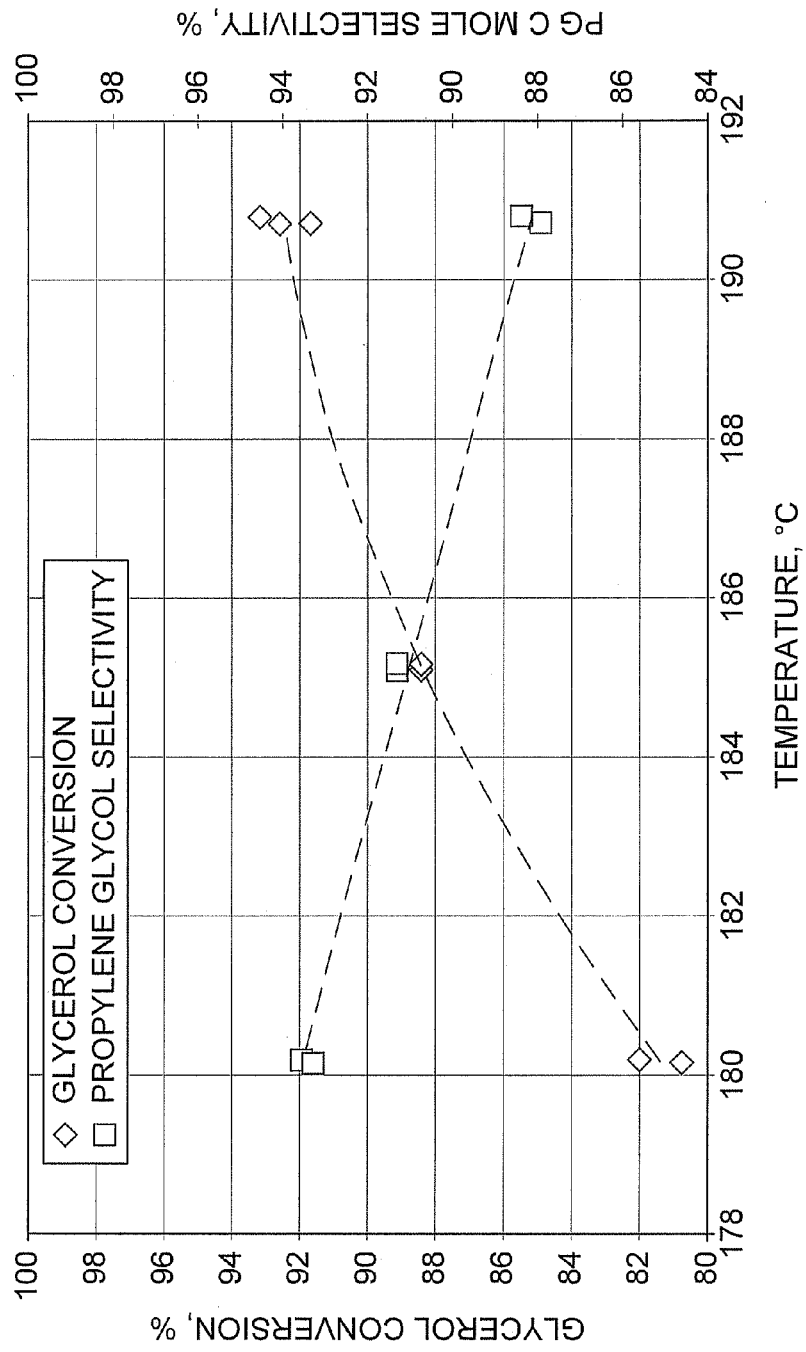
FIGS. 2-3 are plots demonstrating the impact of reactor temperature on glycerol conversion, propylene glycol selectivity and byproduct selectivity.

The catalyst from Example 1 above was loaded in the pilot plant described in Example 1. Glycerol feed 1 from Table 1 above was also used. The purpose of this test was to evaluate the impact of varying reactor temperature on glycerol conversion and product selectivities. In this test, the reactor pressure was 1200 psig, the LHSV was 1.17 hr$^{-1}$, the H$_2$/glycerol molar feed ratio was 5.0 and the pH of the glycerol feed was adjusted with 1.0 wt % NaOH. The reactor temperatures were varied from 356-374° F. (180-190° C.). This relatively small change in the reaction temperature had a very significant effect on the catalyst performance as shown in Table 2 below and in FIGS. 2-3.

TABLE 2

| | Temperature, ° C. | | |
|---|---|---|---|
| | 180 | 185 | 190 |
| Glycerol Conversion, % | 81.4 | 88.4 | 92.5 |
| Propylene Glycol Selectivity, C mol % | 93.4 | 91.3 | 88.1 |
| Ethylene Glycol Selectivity, C mol % | 2.6 | 2.8 | 3.1 |
| Butanediol Selectivity, C mol % | 0.5 | 1.0 | 1.9 |

Figure 3:
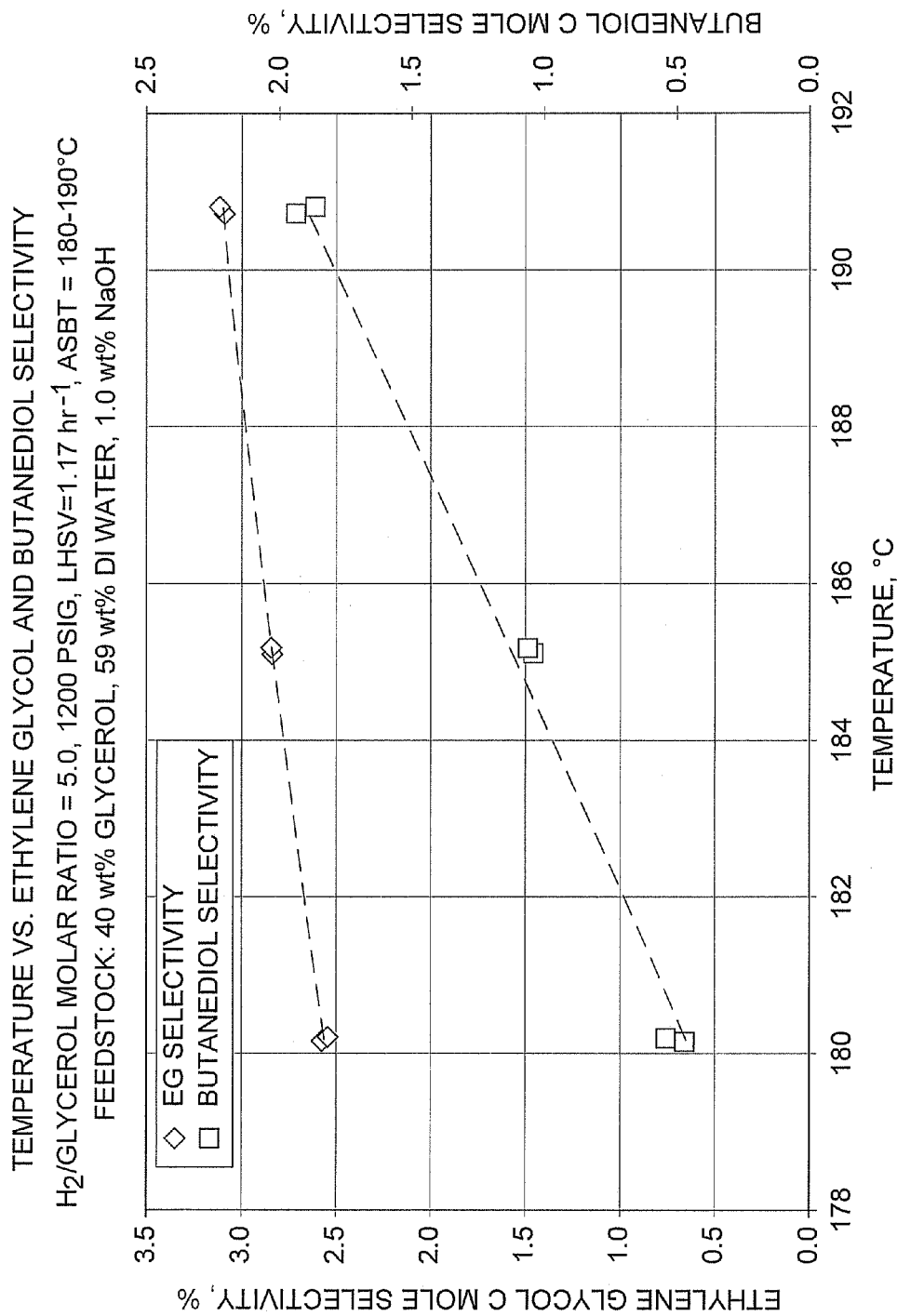

To summarize the tabulated results, the glycerol conversion decreased from ~92.5% to ~81.4% as the temperature was decreased from 374° F. to 356° F. (180-190° C.). However, the propylene glycol selectivity increased from ~88.1 C mol % to ~93.4 C mol %. More importantly, operating at 356° F. (180° C.) rather than 374° F. (190° C.) had a significant impact on the byproduct production. Both the 2,3-butanediol selectivity and ethylene glycol selectivity were lower at lower temperature. Indeed, as shown in FIG. 3, the ethylene glycol C mole % selectivity was over 3 at 190° C. and dropped to about 2.6 at 180° C. Similarily, the butanediol C mole % selectivity was nearly 2 at 190° C. and dropped significantly to below 1.0 at 180° C. This result demonstrates that minimizing the increase in temperature of reactants across the fixed bed of catalyst will have a very beneficial impact on minimizing unwanted byproduct production and maximizing propylene glycol yields. In this case, the amount of the byproducts with boiling points close to the boiling point of propylene glycol (e.g., butanediols) are low enough that the propylene glycol product can be sold as-is without requiring a polishing step to separate the close boiling butanediols from the propylene glycol.

EXAMPLE 3

The purpose of this example was to determine if there was any detrimental impact on catalyst performance by operating the reactor at increased H$_2$:glycerol ratios that could be present in a hydrogen gas quenched reactor. This example used the catalyst of Example 1 and glycerol feed 1 from Table 1 in the pilot plant of Example 1. The pilot plant reactor was operated at conditions including a pressure of 1200 psig, an LHSV of 1.17 hr$^{-1}$, and a temperature of 356° F. The glycerol feed pH was adjusted to 12 with a 1.0 wt % solution of NaOH.

Figure 4:
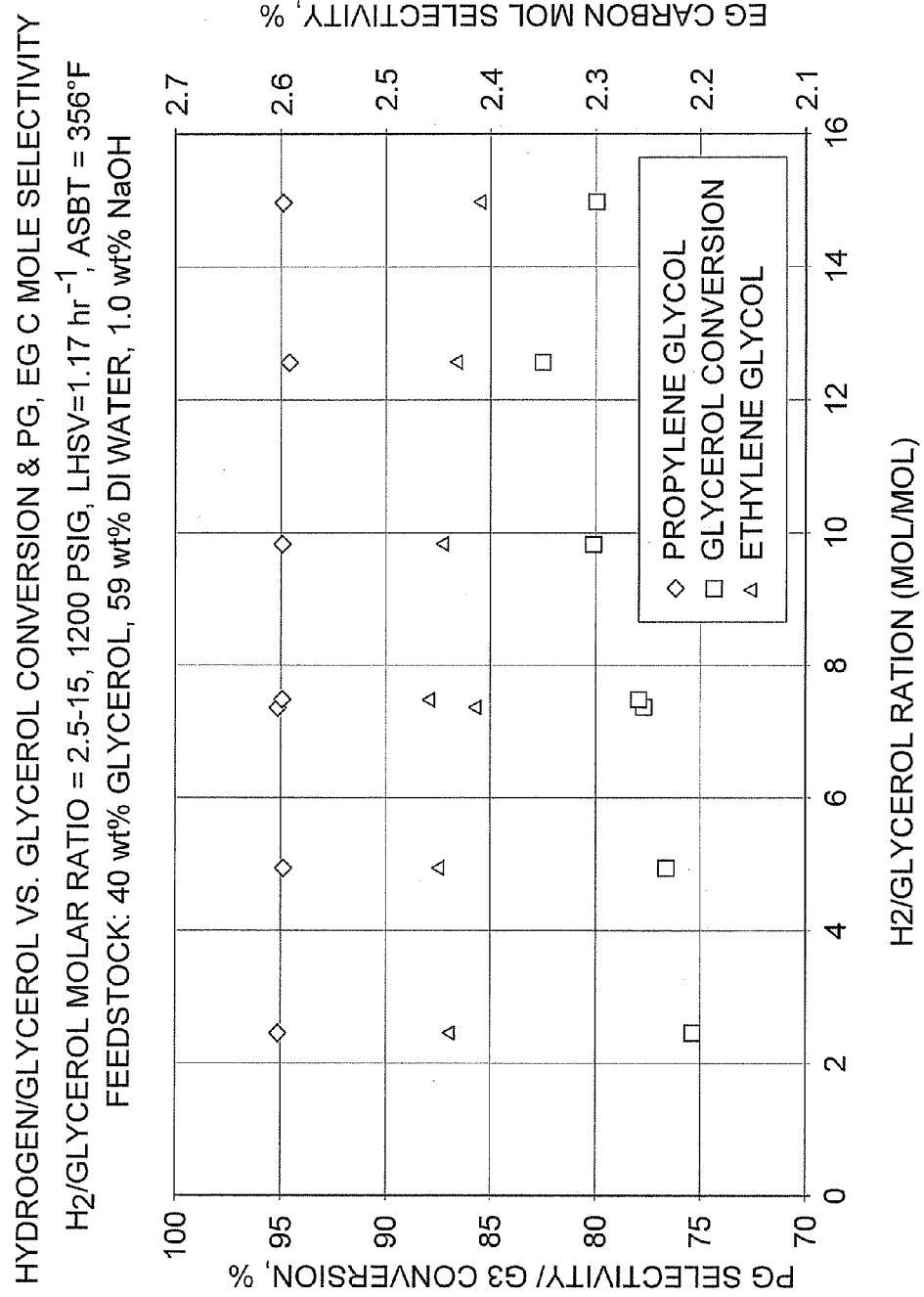
FIG. 4 is a plot demonstrating the impact of varying feed $H_2$/glycerol ratios on glycerol conversion and product yields.

The H$_2$/glycerol ratios were varied from 2.5-15 mol/mol. A plot of the results of varying this ratio on glycerol conversion and product yields is found at FIG. 4. The plotted results demonstrate that increasing the amount of hydrogen in the reactor feed had little impact on propylene glycol selectivity and actually improved glycerol conversion slightly while reducing ethylene glycol selectivity. This result shows that hydrogen can be used as a quench gas without having a detrimental impact on reaction product selectivities or glycerol conversion.

The invention claimed is:

1. An apparatus for converting glycerol into propylene glycol, the apparatus comprising:
   a feed stream comprising a hydrogen containing gas and a glycerol feed that includes at least 30 wt % of glycerol;
   a reactor comprising at least two catalyst beds and a quench mixing zone, wherein the at least two catalyst beds includes two adjacent catalyst beds that are separated from each other by the quench mixing zone, and wherein the reactor is configured to receive the feed stream and to operate at glycerol conversion conditions effective to convert glycerol into propylene glycol; and
   a conduit for directing a quench material into the quench mixing zone to limit a temperature from increasing across at least one of the two adjacent catalyst beds by more than about 80° F.

2. The apparatus of claim 1 wherein the quench material is a gas.

3. The apparatus of claim 2 wherein the quench material is selected from that group consisting of a make-up hydrogen containing gas, a recycle hydrogen containing gas, and combinations thereof.

4. The apparatus of claim 3 wherein the quench material includes the make-up hydrogen containing gas.

5. The apparatus of claim 3 wherein the quench material includes the recycle hydrogen containing gas.

6. The apparatus of claim 1 wherein the quench material is a liquid.

7. The apparatus of claim 6 wherein the quench material is selected from the group consisting of a basic glycerol feed, water, recycle water from the product purification section, unconverted glycerol from the product purification section, a high pressure separator liquid product, any product or byproduct stream recovered in a product purification section, and combinations thereof.

8. The apparatus of claim 1 wherein the reactor further comprises a third adjacent catalyst bed, an additional quench mixing zone that separates the third adjacent catalyst bed from the two adjacent catalyst beds, and an additional quench stream that is directed into the additional quench mixing zone.

9. A method for converting glycerol into propylene glycol, the method comprising the steps of:
   directing a basic glycerol containing feed stream and a hydrogen containing gas to a reactor that comprises at least two catalyst beds including two adjacent catalyst beds that are separated by a quench mixing zone, wherein the reactor is operating at glycerol conversion conditions effective to form a reactor product including propylene glycol; and
   directing a quench material into the quench mixing zone to limit a temperature from increasing across at least one of the two adjacent catalyst beds by more than 80° F.

10. The method of claim 9 wherein the quench material is a gas.

11. The method of claim 10 wherein the quench material is selected from that group consisting of a make-up hydrogen containing gas, a recycle hydrogen containing gas, and combinations thereof.

12. The method of claim 9 wherein the quench material is a liquid.

13. The method of claim 12 wherein the quench material is selected from the group consisting of a basic glycerol feed, water, recycle water from the product purification section, unconverted glycerol from the product purification section, a high pressure separator liquid product, any product or byproduct stream recovered in a product purification section, and combinations thereof.

14. The method of claim 9 wherein the reactor further comprises a third adjacent catalyst bed and an additional quench mixing zone that separates the third adjacent catalyst bed from the two adjacent catalyst beds.

15. The method of claim 9 wherein the step of directing the quench material includes limiting the temperature from increasing across the at least one of the two adjacent catalyst beds from about 10 to about 40° F.

16. The method of claim 9 wherein the quench material is make up hydrogen or recycle gas and wherein a reactor $H_2$/glycol ratio at a reactor outlet is from about 2 to about 20 mole/mole.

17. The method of claim 9 wherein the reactor is operating at a temperature that does not exceed about 374° F. at an inlet corresponding to each of the at least two catalyst beds.

18. The method of claim 9 wherein the glycol conversion conditions include maintaining each of the at least two catalyst beds at an inlet temperature and temperature differential across each of the at least two catalyst beds effective to maintain a butanediol C mole % selectivity to less than about 1.

* * * * *